(12) United States Patent
Bestebreurtje

(10) Patent No.: US 10,422,773 B2
(45) Date of Patent: Sep. 24, 2019

(54) MOBILE ULTRASONIC RAIL INSPECTION SYSTEM AND METHOD

(71) Applicant: Sonimex B.V., Tiel (NL)

(72) Inventor: Pieter Bestebreurtje, Tiel (NL)

(73) Assignee: Sonimex B.V., Tiel (NL)

( * ) Notice: Subject to any disclaimer, the term of this patent is extended or adjusted under 35 U.S.C. 154(b) by 295 days.

(21) Appl. No.: 15/127,027

(22) PCT Filed: Mar. 17, 2015

(86) PCT No.: PCT/NL2015/000012
§ 371 (c)(1),
(2) Date: Sep. 18, 2016

(87) PCT Pub. No.: WO2015/142163
PCT Pub. Date: Sep. 24, 2015

(65) Prior Publication Data
US 2017/0108473 A1    Apr. 20, 2017

(30) Foreign Application Priority Data

Mar. 17, 2014  (NL) ........................................ 1040728
Oct. 10, 2014  (NL) ........................................ 1040991

(51) Int. Cl.
*G01N 29/34*     (2006.01)
*G01N 29/07*     (2006.01)
(Continued)

(52) U.S. Cl.
CPC ........... *G01N 29/343* (2013.01); *G01N 29/07* (2013.01); *G01N 29/2493* (2013.01);
(Continued)

(58) Field of Classification Search
CPC .. G01N 29/343; G01N 29/07; G01N 29/2493; G01N 29/28; G01N 29/265;
(Continued)

(56) References Cited

U.S. PATENT DOCUMENTS 4,174,636 A    11/1979  Pagano
4,487,071 A    12/1984  Pagano et al.
(Continued)

FOREIGN PATENT DOCUMENTS

DE    102004026995 A1    7/2006
JP    S58151554 A        9/1983

OTHER PUBLICATIONS

International Search Report and Written Opinion of the International Search Authority for PCT/NL2015/000012, dated Sep. 15, 2015.

*Primary Examiner* — Natalie Huls
*Assistant Examiner* — Suman K Nath
(74) *Attorney, Agent, or Firm* — Troutman Sanders LLP; Ryan A. Schneider; Christopher C. Close, Jr.

(57) ABSTRACT

An ultrasonic rail inspection system includes an ultrasonic transducer mounted on a yoke for attachment to a frame of a rail inspection vehicle. The ultrasonic transducer transmits ultrasonic pulses and receives reflected ultrasonic pulses. A control device controls the ultrasonic transducer. A clock device provides clock signals to the control device. The control device controls the ultrasonic transducer to transmit the ultrasonic pulses at a fixed pulse repetition period.

7 Claims, 5 Drawing Sheets

(51) Int. Cl.
   *G01N 29/24*   (2006.01)
   *G01N 29/28*   (2006.01)
(52) U.S. Cl.
   CPC ....... *G01N 29/28* (2013.01); *G01N 2291/011* (2013.01); *G01N 2291/0234* (2013.01); *G01N 2291/0289* (2013.01); *G01N 2291/044* (2013.01); *G01N 2291/2623* (2013.01)
(58) Field of Classification Search
   CPC .. G01N 29/36; G01N 29/04; G01N 2291/011; G01N 2291/0234; G01N 2291/0289; G01N 2291/044; G01N 2291/2623; G01N 2291/4427
   USPC ............................ 73/625, 639, 635, 636, 644
   See application file for complete search history.

(56)              References Cited

U.S. PATENT DOCUMENTS

| | | | | |
|---|---|---|---|---|
| 5,216,622 | A * | 6/1993 | Kibblewhite | G01L 5/246 |
| | | | | 700/275 |
| 6,161,435 | A * | 12/2000 | Bond | B01D 61/12 |
| | | | | 210/785 |
| 2006/0117855 | A1 | 6/2006 | Barshinger et al. | |
| 2009/0133501 | A1* | 5/2009 | Georgeson | G01N 29/04 |
| | | | | 73/632 |
| 2012/0177257 | A1* | 7/2012 | Maev | A61B 5/1172 |
| | | | | 382/124 |
| 2012/0194543 | A1* | 8/2012 | Sato | H04N 1/00506 |
| | | | | 345/619 |

* cited by examiner

MOBILE ULTRASONIC RAIL INSPECTION SYSTEM AND METHOD

FIELD OF THE INVENTION

The present invention relates in general to the art of detecting flaws, particularly cracks, in railroad rails.

BACKGROUND OF THE INVENTION

For safety reasons, it is important that railroad rails are inspected regularly for the presence of flaws or defects. A flaw or defect may be an existing small crack, or a location where a crack could arise. Cracks have the tendency to grow, and a broken rail may have catastropic consequences, so it is important to detect potential crack sites as early as possible. Many cracks are rarely visible from the outside; if they are, the rail is probably completely broken, and this is a situation that is to be avoided. Hence, a technology is required that is capable of detecting flaws in the rail.

Such technology is ultrasonic measurement. Briefly said, an ultrasonic pulse is coupled into the rail, and the reflection of this pulse is captured. The pulse reflects from material surfaces, such as the outside rail surface but also the internal surface of a flaw. Thus, the reflection pattern in the case of a flaw differs from the reflection pattern in the case of an undisturbed rail. However, although the measurements could be performed stationary from a technical point of view, this is not desirable from a practical point of view, because the railroad should remain open for railroad traffic. Therefore, mobile systems have been developed that include a railroad vehicle carrying a mobile ultrasonic transducer.

Such mobile systems, however, introduce the complication that the ultrasonic transmitter and the ultrasonic receiver are moving with respect to the rail under inspection. One aspect of this complication is that it is more complicated to achieve a good signal coupling between rail and transducer. Another aspect of this complication is that the pulse measurement itself requires some measuring time, basically caused by the travelling time of the pulse from the ultrasonic transmitter to the reflection surface and back to the ultrasonic receiver. This sets restrictions on the minimum repetition frequency of the measurements. On the other hand, the repetition frequency of the measurements, or better: the time period between successive measurements, determines the spatial distance between the investigated rail locations, indicated as "inspection pitch". With a certain maximum requirement for the inspection pitch (i.e. the pitch should be a certain value or shorter), a certain maximum operational speed for the inspection vehicle results (i.e. the operational speed can not be higher than a certain value). Given the fact that the railroad tends to be used more and more intensely, with regular trains driving faster and/or at closer mutual distance, it is desirable that the maximum operational speed for the inspection vehicle is as high as possible. If the inspection vehicles are too slow, they either disrupt regular service, or inspection can be done only during the night when traffic is reduced.

Mobile ultrasonic rail inspection systems can be distinguished in two basically different types. Both types require a liquid coupling substance between the ultrasonic transducer and the rail. A first type of inspection system is indicated as a contact-type system: in these systems, the transducer is held at a small distance from the rail, with a thin film of coupling liquid in between. A drawback of this type of system is the relatively large consumption of coupling liquid. This drawback is avoided in the second type of inspection system, which is indicated as a wheel-type system (or a "rotating" rail riding system): in these systems, the transducer is positioned inside a wheel-like container filled with coupling liquid and riding on the rail, which wheel-like container has a flexible wall that is able to conform to the shape of the rail head.

In practical circumstances, with an inspection pitch of about 3 mm, the maximum operational speed for the inspection vehicle is about 72 km/h for the contact-type system and about 37 km/h for the wheel-type system.

SUMMARY OF THE INVENTION

An object of the present invention is to improve on the existing technology so that the maximum operational speed for the inspection vehicle can be substantially increased or the inspection pitch can be reduced, or both. The principle proposed by the present invention is applicable in each type of wheel-type inspection system, and will result in an improvement in each system as compared to the capabilities of such system without the invention, ceteris paribus, but the extent of the improvement may depend on the actual system.

BRIEF DESCRIPTION OF THE DRAWINGS

These and other aspects, features and advantages of the present invention will be further explained by the following description of one or more preferred embodiments with reference to the drawings, in which same reference numerals indicate same or similar parts, and in which.

DETAILED DESCRIPTION OF THE INVENTION

Figure 1A:
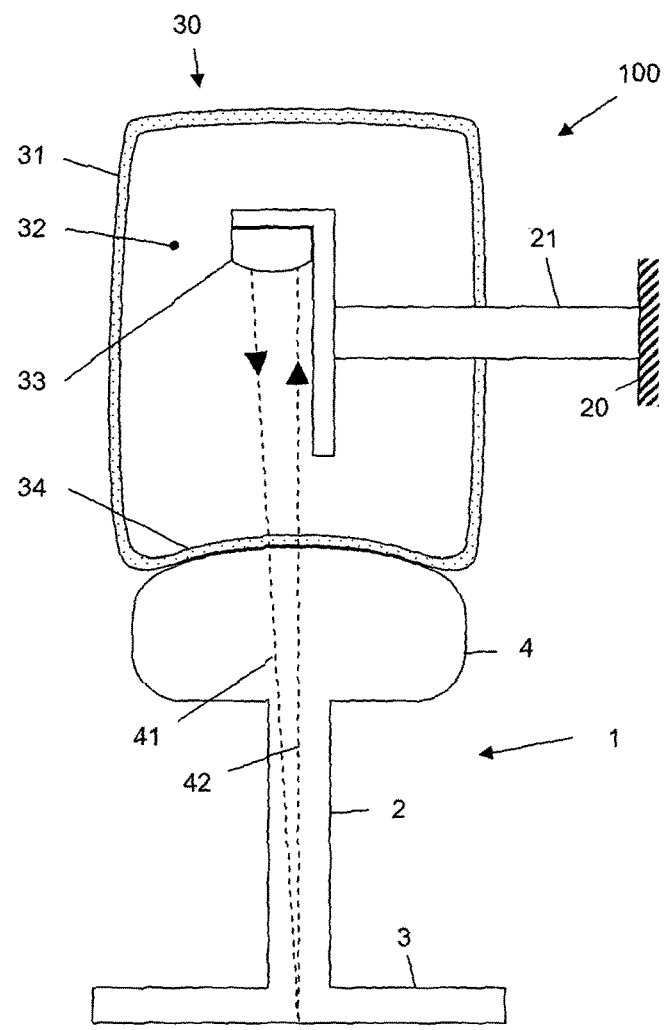
FIG. 1A is a schematic cross-section of an ultrasonic rail inspection system.

FIG. 1A schematically shows a cross-section of a rail 1, having a central rail body or web 2, a rail foot 3 and a rail head 4. A rail inspection vehicle 100 comprises a yoke 21 mounted to a frame 20. The vehicle 100 comprises an ultrasonic rail examination system 30, which includes at least one ultrasonic transducer 33 mounted on the yoke 21 within a rotating rail riding container 31 filled with coupling liquid 32, typically water or glycol or a mixture thereof. The rail riding container 31 is pressed onto the rail head 4. The wall of the container 31 is flexible, at least to a certain extent, so that the container wall conforms to the top surface of the rail head 4. A contact area of the container wall is indicated at 34. With travel of the vehicle 100 over the rail 1, the rotating container 31 rolls over the rail and is therefore also indicated as "wheel". For a more detailed description of an example of such wheel-type system, reference is made to U.S. Pat. No. 5,419,196 by way of example.

Figure 1B:
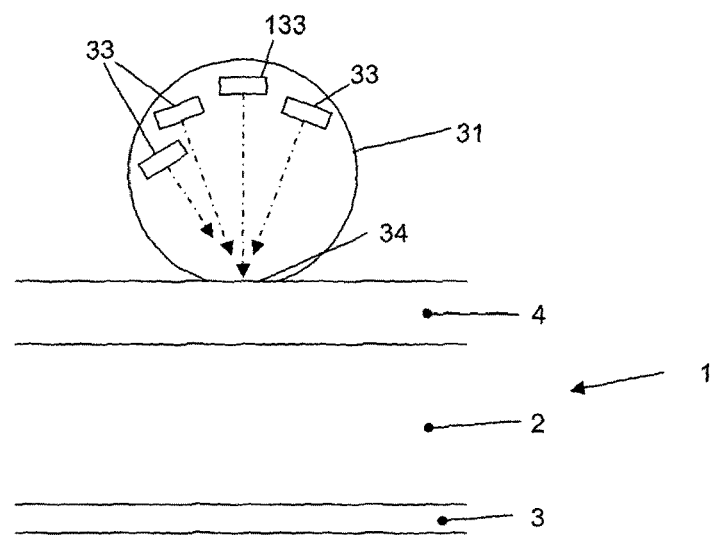
FIG. 1B schematically illustrates the disposition of several transducers in an ultrasonic rail inspection system.

It is noted that the figure only shows one transducer 33, but in practice the rotating rail riding system 30 may comprise multiple transducers, directed to the rail 1 under different angles. FIG. 1B is a schematic side view of the wheel 31 on the rail 1, showing multiple transducers 33 positioned within the wheel 31. It can be seen that the transducers aim their ultrasonic beams 41 to the same contact area 34 under different angles. These angles are standardised; typical angles are 0°, 40°, 70°, as will be known to persons skilled in the art. And transducers may look forward or backward.

The basic operation is as follows. At a certain moment in time, the transducer 33 sends an ultrasonic pulse 41 into the rail head 4 via the contact area 34. The ultrasonic pulse 41 reflects from a reflective surface within the rail 1. The reflected pulse 42 is received by the transducer 33. The reflective surface may be the bottom of the rail foot 3, as shown in the figure, but may also be a flaw such as for instance a crack.

Figure 2:
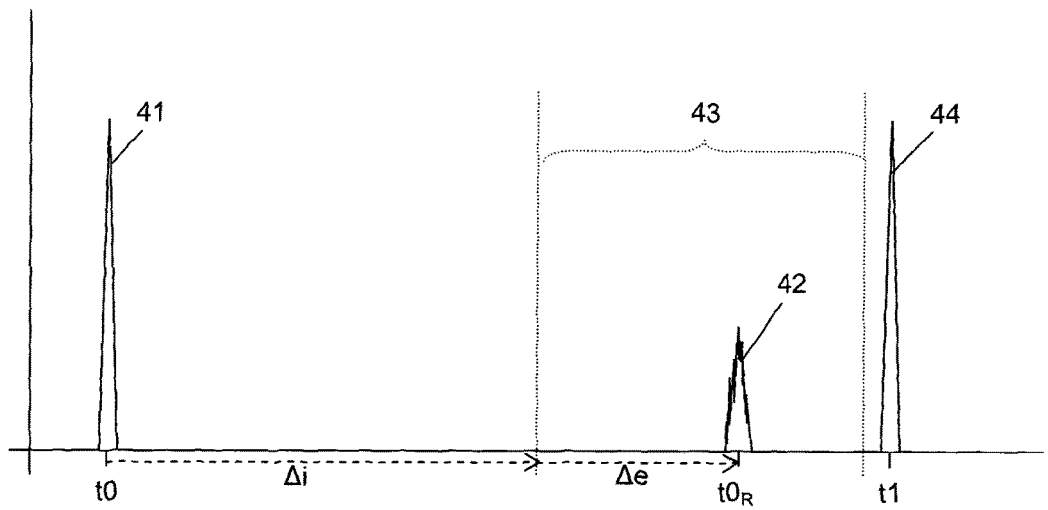
FIG. 2 is a graph showing ultrasonic signals as a function of time.

FIG. 2 is a graph showing the ultrasonic signals as a function of time. The horizontal axis represents time, the vertical axis represents signal strength, in arbitrary units. At time t0, the transducer 33 sends the ultrasonic pulse 41 to the rail head 4. At time t0R, the reflected pulse 42 is received by the transducer 33.

The distance between transducer 33 and contact area 34 may be in the order of about 135 mm. The sound velocity in the medium 32 is in the order of about 1700 m/s. Consequently, the travel time of the pulses 41 and 42 in the medium 32 is in the order of about 160 μs. This travel time will be indicated as internal delay $\Delta i$.

In the rail 1, the sound velocity is in the order of about 5900 m/s for the longitudinal mode and in the order of about 3200 m/s for the transversal mode. The travel distance (back and forth) in the rail depends on the angle of the ultrasonic beam and on the presence of defects. Theoretically, the travel distance can be zero. Without defects, the travel distance for instance for a 40° transducer may be in the order of 450 mm, in which case the travel time of the pulses 41 and 42 in the rail is in the order of about 140 μs for the transversal mode. This travel time will be indicated as external travelling time $\Delta e$. Thus, the total time lapse $\Delta t = \Delta i + \Delta e$ from t0 to t0R may vary within a reflection range 43 from 160 to 300 μs. The width of this reflection range 43 corresponds to the maximum expected external travelling time $\Delta e_{MAX}$.

It should be clear to a person skilled in the art that the above calculation is given by way of example, and that the precise values for a given concrete system may deviate depending on the precise system design.

When performing a rail inspection, there may be requirements or regulations defining the defect resolution. A typical required maximum pitch is 3 mm, which basically means that the ultrasonic pulses should be transmitted for each 3 mm of travel progress of the vehicle. In the currently practiced art, the vehicle is provided with a sensor that very accurately measures the travel distance of the vehicle, and that sends a trigger pulse to the ultrasonic transducer after a predetermined distance, for instance a trigger pulse for every 1, 2 or 3 mm of progress. However, a subsequent ultrasonic transmission pulse 44 at time t1 should not interfere with the reflection pulses, which can be expected up to 300 μs from the previous ultrasonic transmission pulse. This means that the trigger pulses may not be less than 300 μs apart. In the example of a 3 mm inspection pitch, this translates to a maximum vehicle speed of 37 km/h.

Figure 3:
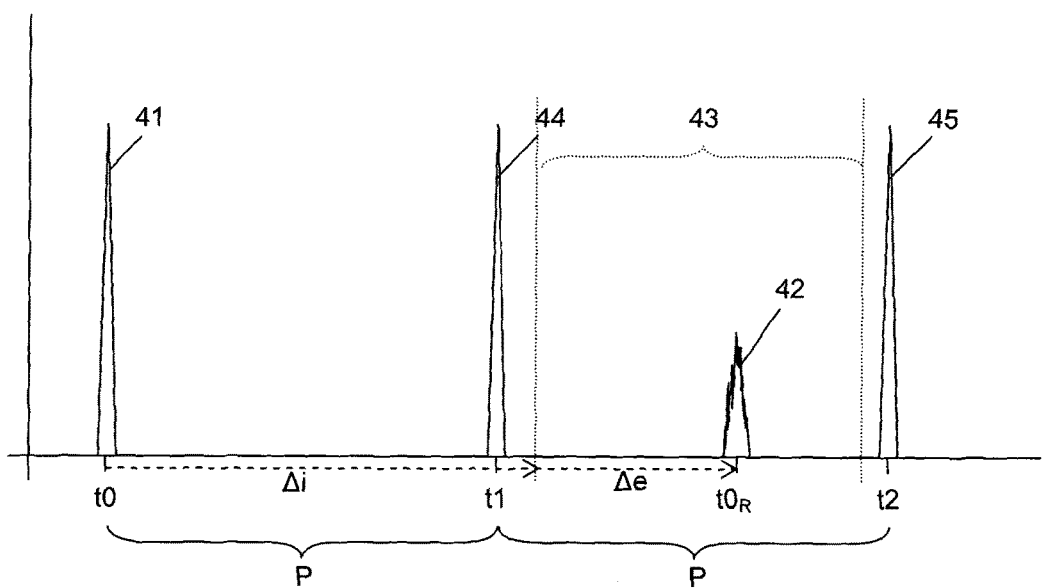
FIG. 3 is a graph showing ultrasonic signals as a function of time.

FIG. 3 is a graph comparable to FIG. 2, showing the ultrasonic signals as a function of time for a system proposed by the present invention. Instead of transmitting the subsequent ultrasonic transmission pulse 44 after termination of the reflection range 43, the present invention proposes to transmit the subsequent ultrasonic transmission pulse 44 at time t1 before start of the reflection range 43. Further, instead of triggering the ultrasonic transducer by trigger pulses derived from a travel distance measurement, the ultrasonic transducer is fired at a constant repetition frequency, or in other words at a constant repetition period t1−t0=P.

FIG. 3 also shows a next subsequent ultrasonic transmission pulse 45 at time t2=t0+2P. The figure illustrates that the key of the present invention is that the reflection range associated with an N-th transmission pulse is always located between the (N+1)th and (N+2)th transmission pulses. It will be seen that the following formulas apply:

$$P \leq \Delta i \quad (1)$$

$$2P \geq \Delta i + \Delta e_{MAX} \quad (2)$$

From these formulas, it follows that the maximum expected external travelling time $\Delta e_{MAX}$ should be smaller than the internal delay $\Delta i$, and that the ultrasonic pulse repetition period P can be set in the range from $(\Delta i + \Delta e_{MAX})/2$ to $\Delta i$. In practice, it may be that the compression of the container 31 varies during the travel of the vehicle. This will have as consequence that the internal delay $\Delta i$ varies. In order to accommodate for this variation, it may be preferred that P be set in the centre of said range.

For the example as described above, with $\Delta i$=160 μs and $\Delta e_{MAX}$=140 μs, a preferred value for the ultrasonic pulse repetition period P would be 155 μs. This means that a 3 mm inspection pitch will be achieved at a vehicle speed of about 70 km/h.

It is noted that JP-58151554 discloses a method for detecting defects in the bottom part of a railroad rail. An ultrasonic pulse a1 is emitted into the rail under a certain angle, and will reflect from the rail bottom as bottom pulse b1. In case there is no defect, this bottom pulse b1 will not reach the ultrasonic transducer. In case there is a defect, the pulse will reflect from the defect as reflected pulse c1 towards the transducer. The time duration between emission of a1 and detection of c1 is indicated as TE. The document discloses that the next ultrasonic pulse a2 is emitted before the reflected pulse c1 reaches the transducer. The time between a1 and a2 is indicated as T, and the formula T<TE applies. Further, the formula 2T>TE applies. However, the document does not specify a wheel-type inspection system, consequently does not mention the travel of the sound wave in the liquid medium of the inspection wheel, and is silent about any reflection originating from the upper surface of the rail. More particularly, the document does not specify that the next ultrasonic pulse a2 should be transmitted before detection of the reflection originating from the upper surface of the rail.

Figure 4:
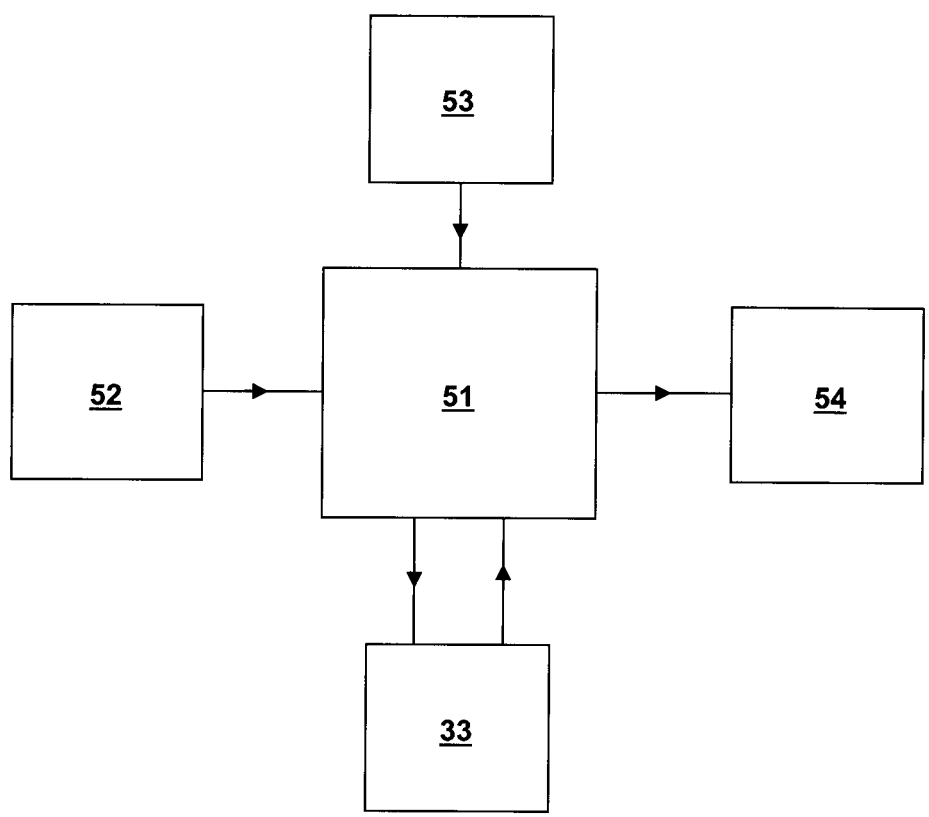
FIG. 4 is a schematic block diagram of an ultrasonic rail inspection system.

FIG. 4 is a schematic block diagram of the ultrasonic rail examination system 30 according to the present invention. Reference numeral 51 indicates a control device, for instance a suitably programmed microprocessor.

Reference numeral 52 indicates a clock, for providing clock signals to the control device 51. The clock 52 may be an external component to the control device 51, but may also be an integrated component of the control device 51. On the basis of the clock signals, the control device 51 is designed to provide trigger signals for the transducer 33 at a predetermined pulse repetition period P.

Reference numeral 53 indicates a sensor for sensing travel distance of the vehicle 100. Such sensor may for instance include a tachometer for sensing rotation angle of a wheel axle of the vehicle 100. The sensor output signal is provided to the control device 51.

Reference numeral 54 indicates an output device. The output device may include for instance a printer, a plotter, a display monitor, a memory. The control device 51 is programmed to generate an output signal that contains information from the ultrasonic reflection signal received from the transducer 33 in conjuction with the location information (distance along the rail) as obtained from the travel distance sensor 53. The information from the ultrasonic reflection signal received from the transducer 33 may include the original receipt signal as received by the transducer 33, or a processed signal that shows artefacts. In conjunction with the distance information received from sensor 53, the control device 51 may translate the ultrasonic reflection signal to a displayed signal as function of location. Use of the sensor 53 allows the vehicle to be driven at varying speed: at lower speed, the displaced signals will be closer together and at higher speed they will be further apart, but they will at all times be correlated to distance, which is very intuitive for the personnel using the system.

Although the above explanation contains a description for a single transducer 33 only, it should be clear that the same explanation applies to a system that comprises two or more transducers.

Figure 5:
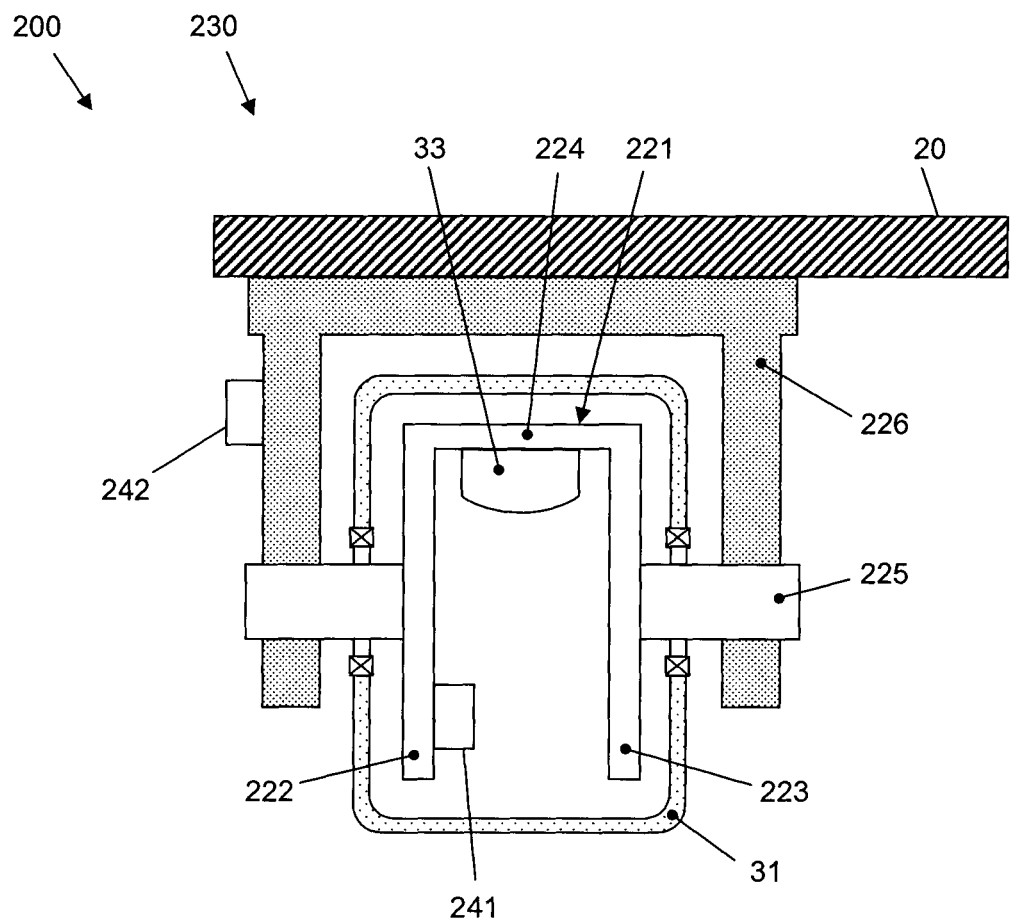
FIG. 5 is a schematic cross-section of an ultrasonic rail inspection system.

FIG. 5 is a schematic cross-section of an ultrasonic rail inspection system 230 of a rail inspection vehicle 200. For the ultrasonic rail inspection system 230, the same explanation as above may apply. The figure shows a transducer 33 mounted on a carrier 221 that has an inverted U-shape with arms 222, 223 and a bridge 224. The arms 222, 223 are connected to two aligned halves of a horizontal shaft 225. The wheel 31 rotates around the shaft 225. The ends of the shaft 225 are mounted in a frame mount 226 having an inverted U-shape and being attached to vehicle frame 20. It is noted that the system comprises a plurality of transducers, but the figure only shows one for sake of simplicity.

It is easily possible to exchange the set of transducers: by detaching the frame mount 226 from the vehicle frame 20, the entire unit of frame mount 226, shaft 225, carrier 221, transducers 33, container 31 with liquid 32 can be removed and a different unit can be mounted in place. When mounting such unit, it is important that the unit is mounted in the correct orientation: the transducers should have correct orientations with respect to the rail. Each transducer is designed to direct an ultrasonic beam to the contact area 34 between container 31 and rail head 4 under a specific angle to detect specific artefacts at specific locations within the rail 1, and a mis-alignment of the carrier 221 will result in mis-alignment of the transducers 33 which in turn may result in corrupted measuring results. It is customary that the transducers are adjusted with respect to a rail: for instance, the alignment is adjusted until the 0° transducer shows a maximum in reception strength, which indicates that the beam is perpendicular to the rail. However, practical rails are hardly suitable for performing such adjustment, and therefore this alignment needs to be done in a laboratory setting with a special test rail portion. This is very cumbersome.

In order to provide a solution to this problem, the present invention proposes to attach a first 3D-gyrosensor 241 to the carrier 221 and a second 3D-gyrosensor 242 to the frame mount 226. In an adjustment situation, which may be in a laboratory setting and which does not require the presence of a train, the transducers are aligned accurately with respect to the carrier 221, and the carrier 221 is aligned with respect to the frame mount 226 using the first gyrosensor 241. The second gyrosensor 242 is now set to zero. Consequently, whenever the second gyrosensor 242 shows a zero-reading, it is certain that the transducers 33 are aligned correctly.

When this unit is mounted on an inspection vehicle, it may be that the mounting accommodation of the vehicle is not aligned accurately. This may show as a deviation of the second gyrosensor 242, and can be compensated by adjusting the mounting of the frame mount 226 to the vehicle frame 20 until the second gyrosensor 242 shows a level reading.

In the following, a variation of the present invention will be discussed.

As mentioned before, the system typically comprises multiple transducers, and one of these transducers typically is the so-called 0°-transducer, which is a transducer that sends its ultrasonic beam 41 vertically downward. In FIG. 1B, this specific transducer is indicated at reference numeral 133. It is typically a transducer for generating longitudinal waves.

Apart from the reflections generated by reflective surface within the rail, there will also be a reflection from the interface between liquid 32 and contact wall area 34 and a reflection from the interface between contact wall area 34 and the top surface of rail head 4. In view of the relatively small thickness of the wall 31, the two reflection pulses resulting from these reflections substantially coincide or at least overlap, and can be considered as one reflection pulse, that is indicated as interface pulse.

Under normal, i.e. flawless conditions, there will subsequently be a reflection from the bottom surface of the rail foot 3, as indicated in FIG. 1A. This reflection will be indicated as bottom pulse. With for instance a rail height of 159 mm, the bottom pulse (longitudinal mode) is typically expected about 54 µs later than the interface pulse. It is noted that the bottom pulse itself will partly reflect from the top surface of rail head 4 and then again reflects from the bottom surface of the rail foot 3, so that a so-called "repeated bottom pulse" is expected 54 µs later than the first bottom pulse. In fact, this repeated reflection up and down will result in a train of pulses 54 µs apart, but each subsequent pulse has an amplitude much smaller than the corresponding previous pulse, so that in practice only the first and second bottom pulse are relevant.

Figure 6:
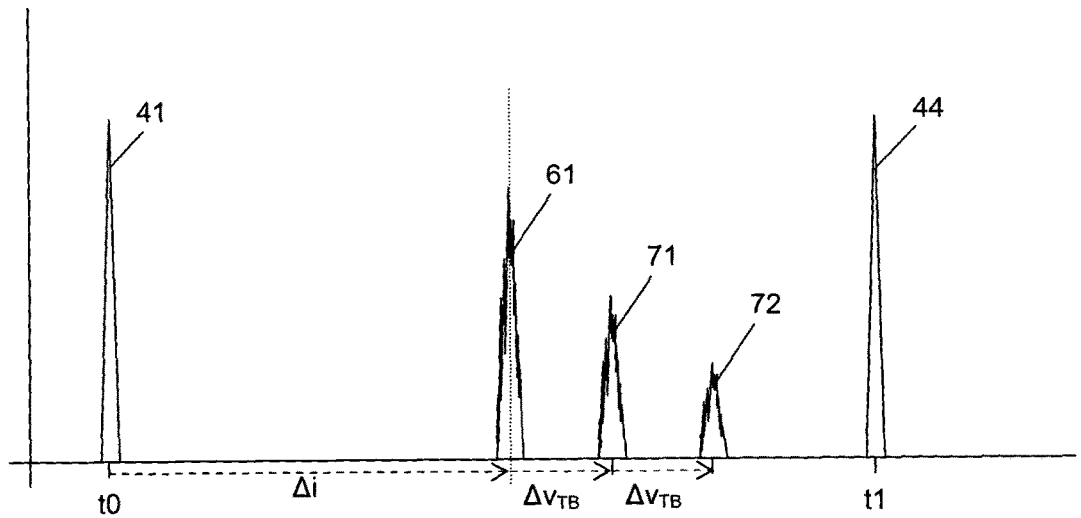
FIG. 6 is a graph comparable to FIG. 2.

FIG. 6 is a graph comparable to FIG. 2, showing the interface pulse at reference numeral 61, showing the bottom pulse at reference numeral 71, and showing the repeated bottom pulse at reference numeral 72. $\Delta v_{TB}$ indicates the travel time from top to bottom of the rail and back along a vertical path. This figure also shows that, in prior art, the subsequent pulse 44 would be transmitted after the train of bottom reflection pulses 71, 72 have been received.

Figure 7:
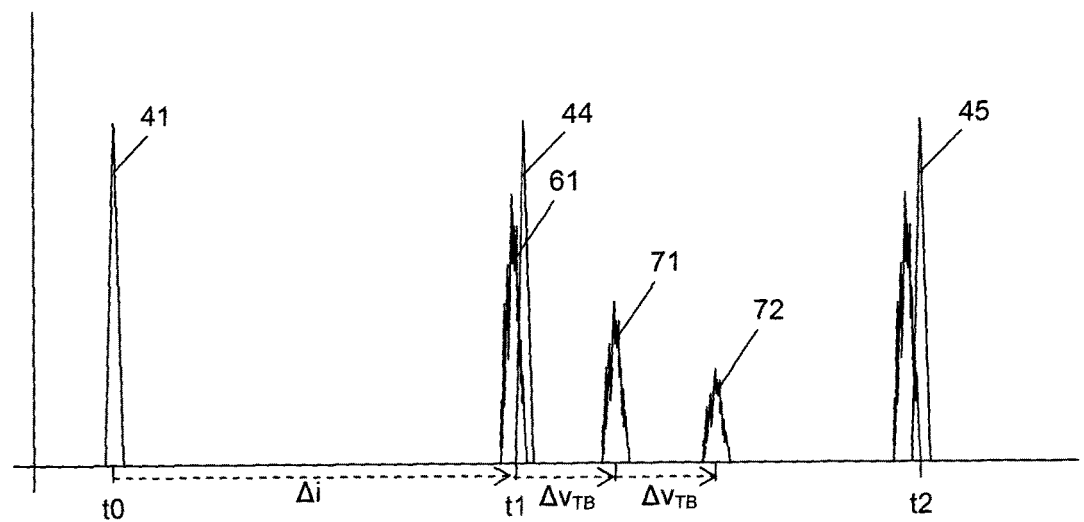
FIG. 7 is a graph comparable to FIG. 3.

FIG. 7 is a graph comparable to FIG. 3, showing a subsequent transmission pulse 44 that largely coincides with the interface pulse 61. This means that the pulse repetition period P is equal to $\Delta i$. It may be that control is set to a pulse repetition period equal to $\Delta i$, but it is also possible that the control device 51 detects the arrival of the interface pulse 61 and in response triggers the transmission of the next pulse. It is noted that all transducers are triggered at the same time.

It is noted that all transducers 33 are preferably arranged along a circular arc around the contact area 34, so that the internal delay $\Delta i$ is equal for all transducers, in which case the control device 51 can simply trigger all transducers at the same time. If needed, timing corrections for the individual transducers 33 can be effected, either in hardware or in software, for instance by displacing a transducer. In any case, the pulse repetition frequency is now determined by the length of the liquid path for the 0°-transducer 133.

It is important to correlate the transmitted/reflected pulse with a specific position on the rail. After all, if a flaw is detected, repair or replacement should be done at the position of the flaw. For this correlation purpose, a tacho sensor is present, giving pulse signals after a certain travel distance, for instance each 0.1 mm. Effectively, each tacho pulse corresponds to a well-defined rail position. The tacho pulses can be input to the control device 51, so that the control device 51, whenever it generates a trigger signal and processes the corresponding reflection signals, can correlate the reflection signals and any possible flaw information contained therein to the tacho signals and the position information contained therein, as should be clear to a person skilled in the art.

In FIG. 7, it will be seen that the bottom reflection pulses 71, 72 from an N-th transmission pulse 41 of the 0°-transducer 133 will be received between the (N+1)th and (N+2)th transmission pulses 44 and 45, i.e. in the time interval needed for the (N+1)th transmission pulse 44 to travel towards the interface contact area 34 and back. The time interval $\Delta v_{TB}$, needed for the longitudinal sound wave to travel from the top surface of the rail to the bottom surface of the rail and back, will obviously depend on the rail geometry. Any reflections from defects or objects in the rail head, web or foot will be received within this time interval.

It should be clear to a person skilled in the art that the present invention is not limited to the exemplary embodiments discussed above, but that several variations and modifications are possible within the protective scope of the invention as defined in the appending claims. For instance, two or more functions may be performed by one single entity, unit or processor. Even if certain features are recited in different dependent claims, the present invention also relates to an embodiment comprising these features in common. Any reference signs in a claim should not be construed as limiting the scope of that claim.

In the above, the present invention has been explained with reference to block diagrams, which illustrate functional blocks of the device according to the present invention. It is to be understood that one or more of these functional blocks may be implemented in hardware, where the function of such functional block is performed by individual hardware components, but it is also possible that one or more of these functional blocks are implemented in software, so that the function of such functional block is performed by one or more program lines of a computer program or a programmable device such as a microprocessor, microcontroller, digital signal processor, etc.

The invention claimed is:

1. An ultrasonic rail inspection system including at least one ultrasonic transducer mounted on a yoke for attachment to a frame of a rail inspection vehicle, wherein one of the at least one ultrasonic transducer is an ultrasonic 0° transducer, wherein the rail inspection system is a rotating rail riding system, wherein each ultrasonic transducer is arranged in a rotating rail riding container filled with coupling liquid and riding on a rail under inspection;
    wherein the ultrasonic 0° transducer is designed to transmit ultrasonic pulses under an angle of 0° with respect to the normal of a contact surface of the rail under inspection, and to receive reflected ultrasonic pulses;
    wherein a control device controls each ultrasonic transducer; and
    wherein the control device is adapted to control the ultrasonic 0° transducer to transmit a next ultrasonic pulse immediately upon receipt of a reflection pulse reflecting from the contact surface of the rail under inspection.

2. The ultrasonic rail inspection system according to claim 1, wherein the system includes a first ultrasonic transducer and a plurality of secondary, non-zero ultrasonic transducers, wherein the first ultrasonic transducer is the ultrasonic 0° transducer;
    wherein the control device is further adapted, immediately upon receipt of the reflection pulse from the contact surface of the rail under inspection and associated with the first ultrasonic transducer, to trigger each secondary ultrasonic transducer to transmit a next ultrasonic pulse; and
    wherein all the secondary ultrasonic transducers are triggered at the same time.

3. The ultrasonic rail inspection system according to claim 2, wherein the distance between the first ultrasonic transducer and the contact surface of the rail under inspection is set such that each secondary ultrasonic transducer transmits its next ultrasonic pulse always before the reflections pulses corresponding to the previous ultrasonic pulses of the respective secondary ultrasonic transducers.

4. The ultrasonic rail inspection system according to claim 1 further comprising:
    a first 3D-gyrosensor; and
    a second 3D-gyrosensor.

5. The ultrasonic rail inspection system according to claim 1, wherein the rail under inspection comprises a rail head upon which the rotating rail riding container rides;
    wherein the rail head has a top surface; and
    wherein the top surface of the rail head is the contact surface.

6. The ultrasonic rail inspection system according to claim 5, wherein each transmitted ultrasonic pulse generates at least two reflected ultrasonic pulses received by the ultrasonic 0° transducer; and
    wherein one of the reflected ultrasonic pulses is the reflection pulse reflecting from the contact surface of the rail under inspection.

7. The ultrasonic rail inspection system according to claim 6, wherein the system includes a first ultrasonic transducer and a plurality of secondary, non-zero ultrasonic transducers, wherein the first ultrasonic transducer is the ultrasonic 0° transducer;
    wherein the control device is further adapted, immediately upon receipt of the reflection pulse from the contact surface of the rail under inspection and associated with the first ultrasonic transducer, to trigger each secondary ultrasonic transducer to transmit a next ultrasonic pulse; and
    wherein all the secondary ultrasonic transducers are triggered at the same time.

* * * * *